United States Patent [19]

Healey et al.

[11] Patent Number: 5,082,651
[45] Date of Patent: Jan. 21, 1992

[54] PHARMACEUTICAL COMPOSITIONS

[75] Inventors: John N. C. Healey, Hitchin; Marshall Whiteman, Baldock, both of England

[73] Assignee: Smith Kline & French Laboratories Limited, Welwyn Garden City, England

[21] Appl. No.: 514,634

[22] Filed: Apr. 25, 1990

[30] Foreign Application Priority Data

Apr. 26, 1989 [GB] United Kingdom ............... 8909559

[51] Int. Cl.$^5$ ...................... A61K 9/12; A61K 31/60; A61K 31/615
[52] U.S. Cl. ....................................... 424/45; 514/166
[58] Field of Search ..................... 514/166; 424/45

[56] References Cited

U.S. PATENT DOCUMENTS

| | | |
|---|---|---|
| 3,866,800 | 2/1975 | Schmitt . |
| 3,997,467 | 12/1976 | Jederstrom . |
| 4,052,986 | 10/1977 | Scaife ................................... 604/212 |
| 4,112,942 | 9/1978 | Scaife ................................... 604/212 |
| 4,211,777 | 7/1980 | Chambers ........................... 514/161 |
| 4,440,763 | 4/1984 | Lover ................................... 514/926 |
| 4,614,736 | 9/1986 | Delevallee et al. ................. 514/179 |
| 4,639,367 | 1/1987 | Mackles ............................... 514/945 |
| 4,657,900 | 4/1987 | Powell et al. ........................ 514/166 |
| 4,752,465 | 6/1988 | Mackles ............................... 514/945 |
| 4,889,709 | 12/1989 | Mackles ............................... 514/945 |
| 4,933,330 | 6/1990 | Jorgensen et al. .................. 514/163 |
| 4,945,084 | 7/1990 | Packman ............................. 514/882 |

FOREIGN PATENT DOCUMENTS 0251462 1/1988 European Pat. Off. .
1304682 1/1973 United Kingdom .
1317771 5/1973 United Kingdom .

Primary Examiner—Shep K. Rose
Attorney, Agent, or Firm—Linda E. Hall; Stuart R. Suter; Edward T. Lentz

[57] ABSTRACT

Pharmaceutical compositions suitable for intra-rectal administration in the form of a foam are described which comprise a therapeutically effective amount of 5-aminosalicylic acid, a pharmaceutically acceptable aqueous carrier therefor, and means for generating a foam.

7 Claims, No Drawings

PHARMACEUTICAL COMPOSITIONS

The present invention relates to a pharmaceutical composition for rectal administration, to a method for its preparation, and to its use in the treatment of ulcerative colitis.

Ulcerative colitis is an inflammatory disease of the colon which is characterised by severe inflammation of the colonic and rectal mucosa and profuse diarrhoea and bleeding. The disease can occur at any age and affects both sexes equally. The prevalence of the disease is greatest in Western society and is estimated to be in the region of 50 to 70 sufferers per 100,000 members of the population—see, for example, the article by P. Baker, The Pharmaceutical Journal, Aug. 6, 1988, page 180.

It is known that sulphasalazine and its metabolite, 5-aminosalicylic acid (5-ASA), are useful in the treatment of ulcerative colitis and a number of products containing these active ingredients are currently sold for this purpose.

A problem with 5-ASA is that it is absorbed in the small intestine and hence, when administered orally, does not reach the colon where it is required to exert a localised topical effect at the site of disease.

Several solutions to this problem have been proposed. One known solution is to administer 5-ASA orally in a polymeric coating which does not break down to release the 5-ASA until the lower ileum/colon is reached. This approach has been described in, for example, U.S. Pat. No. 4,496,553. A drawback with this approach is that, in general, the 5-ASA is delivered to the proximal colon, but may not reach the distal colon in therapeutic concentrations.

Another solution is to administer the 5-ASA directly to the colon by means of rectal administration and it is known to administer 5-ASA in this way by means of suppositories and enemas.

Suppositories suffer from the disadvantage that they show relatively little spreading in the rectum/colon and thus the 5-ASA is not distributed widely throughout the diseased region. Enemas suffer from several disadvantages. Firstly, liquid formulations of 5-ASA are relatively unstable and require special precautions to be taken in order that oxidative decomposition be avoided—see U.S. Pat. No. 4,657,900. Secondly, there is the problem of leakage of the enema liquid from the rectum. Leakage leads not only to a reduction in efficacy of the treatment, since contact time of the 5-ASA with the diseased area is reduced, but can also give rise to the unpleasant problem of stained clothing. The tendency of 5-ASA to acquire a brownish colour when oxidised means that this can be a particular problem.

It has now been found that the above-mentioned problems with existing rectal compositions of 5-ASA can be overcome by administering the 5-ASA in the form of an aqueous foam. The use of a foam overcomes the problem of leakage while allowing the 5-ASA to spread efficiently through the diseased region of the colon.

In a first aspect, therefore, the present invention provides a pharmaceutical composition for intra-rectal administration in the form of a foam which comprises 5-aminosalicylic acid (5-ASA), a pharmaceutically acceptable aqueous carrier therefor and means for generating a foam.

The composition will usually contain at least 15% (w/w) 5-ASA, relative to the total weight of the composition, for example 15% (w/w) to 35% (w/w), and more particularly will contain between 18% (w/w) and 30% (w/w) 5-ASA.

In general the particle size of the 5-ASA will be such that at least 95% of the particles have an equivalent sphere diameter of less than 60μ. The equivalent sphere diameter is the diameter of a sphere having the same volume as the particle; see "Particle Size Measurement", Chapter 4, T. Allen, 2nd Edn., Chapman & Hall, London, 1975.

The means for generating a foam typically comprises a liquid or liquefied gas propellant. Such propellants are well known in the art. In view of the sensitivity of 5-ASA to oxidation, a compressed air propellant is not used. Suitable propellants are hydrocarbons such as propane or butane or halogenated hydrocarbons such as chlorofluorohydrocarbons or fluorohydrocarbons.

Examples of such propellants include the Arcton TM propellants obtainable from Imperial Chemical Industries Limited, Runcorn, Cheshire, U.K., the Freon TM propellants obtainable from Du Pont (U.K.), Stevenage, Hertfordshire, U.K., and the Forane propellants obtainable from Atochem, Paris, France.

Preferably the propellant is selected such that its vapour pressure is in the range from approximately 200 to 350 kNM.$^{-2}$.

A particular propellant is a combination of dichlorodifluoromethane (e.g. Arcton 12) and 1,2-dichlorotetrafluoroethane (e.g. Arcton 114) in the weight ratio 4:6.

The propellant typically is present in the composition in an amount corresponding to between 5% and 15% (w/w), for example approximately 8-10% (w/w).

The carrier typically constitutes from 50% (w/w) to 90% (w/w) of the composition, for example between 55% and 65% (w/w).

The carrier is an aqueous carrier and can contain, in addition to water, a pharmaceutically acceptable water-soluble organic carrier, for example a polyalcohol such as a propylene glycol, glycerol or a polyethyleneglycol and mixtures thereof. The carrier will be one which is compatible with the rectal and colonic mucosa.

In one general embodiment, the carrier contains water in an amount from approximately 20% (w/w) to approximately 100% (w/w) and a water-soluble organic polyalcohol as defined hereinabove, in an amount from approximately 0% (w/w) to approximately 80% (w/w). In a particular embodiment, the carrier contains 50-60% (w/w) water and 40-50% (w/w) polyalcohol.

In order to assist generation of the foam, and to improve the consistency and structure of the composition, it is usual to employ a surfactant. The surfactant chosen will be one which is compatible with the rectal and colonic mucosa and will be present in an amount which achieves the desired pharmaceutical effect but which does not give rise to problems of irritation.

Particularly suitable surfactants are non-ionic surfactants.

Particular surfactants for use in the present compositions are partial esters of sorbitan and sorbitol and their polyoxyethylene derivatives, for example Polysorbate 20 or 80 and Span TM -type surfactants, in particular a mixture of sorbitan mono-oleate and Polysorbate 20.

Suitably the surfactant is present in an amount of up to 15% (w/w) of the composition, preferably less than 12% (w/w).

In order to stiffen the foam, an emulsifying wax will generally be included in the composition. Typical emulsifying waxes for use in the present compositions are non-ionic emulsifying waxes such as those described in the U.S. National Formulary (USNF) and "Martindale". The emulsifying wax described in the USNF is a waxy solid, prepared from cetostearyl alcohol containing a polyoxyethylene derivative of a fatty acid ester of sorbitan. One commercially available emulsifying wax is 'Polawax' which is obtainable from Croda Chemicals Ltd., Goole, U.K.

The emulsifying wax will usually be present in an amount of up to 2% (w/w) of the total weight of the composition, preferably less than 1% (w/w), for example an amount in the range 0.3 to 0.7% (w/w).

The foam compositions will generally have a pH in the range from approximately 4 to 7 and can be buffered or unbuffered. Preferably the compositions are buffered and a particular buffering agent is a mixture of disodium hydrogen orthophosphate and sodium dihydrogen orthophosphate.

The compositions can also contain other ingredients such as preservatives, chelating agents and antioxidants. Typical preservatives are those such as sodium benzoate, sorbic acid and the parahydroxybenzoates, e.g. methylparahydroxybenzoate (methyl paraben) and propylparahydroxybenzoate (propyl paraben). A preferred antioxidant is sodium metabisulphite and advantageously this can be used in conjunction with a chelating agent such as a salt of EDTA, e.g. disodium edetate.

Advantageously the composition contains colloidal silica, for example the Aerosil TM product obtainable from Degussa Ltd. of London, U.K. Suitably the colloidal silica is present in an amount corresponding to less than 1% (w/w); for example it can be present in an amount corresponding to approximately 0.4% (w/w) of the composition.

The compositions of the present invention will usually be presented in a suitable dispensing container, for example an aluminium aerosol container, fitted with a suitable metering valve. Such containers are well known in the art. Where desired, the container can be fitted or supplied together with an applicator device for insertion into the rectum to ensure more efficient administration of the foam.

The compositions of the present invention suitably will be presented in a container fitted with a valve adapted to dispense volumes of from approximately 2 cm$^3$ to approximately 5 cm$^3$. Such valves can be obtained from, for example, Lablabo of 5, Rue Roger Salengro, 92120 Montrouge, France.

The present compositions can be prepared by mixing the ingredients in an appropriate manner and then filling into a suitable dispensing container, for example as described in the Examples.

The compositions of the present invention would typically be used to administer approximately 1-4g of 5-ASA per day, for example by administering one or two doses of 1g 5-ASA once or twice daily. However, the amount administered will depend upon the severity of the condition and ultimately would be at the discretion of the dispensing physician. Where desired, the rectal foams could be used in conjunction with the delayed-release oral preparations of 5-ASA such as the "Asacol" TM product, i.e. the product described in European Patent No. 97651.

Where desired, other therapeutically useful ingredients may be added, for example, steroids such as hydrocortisone and prednisolone.

The invention will now be illustrated by means of Examples.

EXAMPLE 1
FOAM CONCENTRATE
(WITHOUT ADDITION OF PROPELLANT)

|  | % (w/w) | Weight (g) |
|---|---|---|
| 5-Aminosalicylic Acid | 15.0 | 150.0 |
| Polysorbate 80 | 0.25 | 2.5 |
| Emulsifying Wax ('Polawax NF') | 0.5 | 5.0 |
| Colloidal Silicon Dioxide ('Aerosil 200') | 0.5 | 5.0 |
| Sodium Metabisulphite | 0.3 | 3.0 |
| Disodium Edetate, dihydrate | 0.1 | 1.0 |
| Methylparahydroxybenzoate | 0.2 | 2.0 |
| Propylparahydroxybenzoate | 0.04 | 0.4 |
| Disodium Hydrogen Orthophosphate, 12H$_2$O | 1.19 | 11.9 |
| Sodium Dihydrogen Orthophosphate, 2H$_2$O | 0.52 | 5.2 |
| Glycerol | 15.0 | 150.0 |
| Macrogol 300 (Polyethylene Glycol 300) | 15.0 | 150.0 |
| Water, Deionised | 43.4 | 434.0 |

EXAMPLE 2
25% 5-ASA FOAM

|  | % (w/w) | Weight (g) |
|---|---|---|
| 5-Aminosalicylic Acid | 25.0 | 150.0 |
| Sorbitan mono-oleate ('Span 80') | 0.25 | 1.5 |
| Emulsifying Wax ('Polawax NF') | 0.5 | 3.0 |
| Colloidal Silicon Dioxide ('Aerosil 200') | 0.5 | 3.0 |
| Sodium Metabisulphite | 0.3 | 1.8 |
| Disodium Edetate, dihydrate | 0.1 | 0.6 |
| Methylparahydroxybenzoate | 0.2 | 1.2 |
| Propylparahydroxybenzoate | 0.04 | 0.24 |
| Disodium Hydrogen Orthophosphate, 12H$_2$O | 1.19 | 7.14 |
| Sodium Dihydrogen Orthophosphate, 2H$_2$O | 0.52 | 3.12 |
| Glycerol | 15.0 | 90.0 |
| Macrogol 300 | 15.0 | 90.0 |
| Propellants 'Arcton 12/114' 40:60 | 8.0 | 48.0 |
| Water, Deionised | 33.4 | 200.4 |

EXAMPLE 3
25% 5-ASA FOAM CONCENTRATE
(without Addition of Propellant)

|  | % (w/w) | Weight (g) |
|---|---|---|
| 5-Aminosalicylic Acid | 25.0 | 250.0 |
| Emulsifying Wax ('Polawax NF') | 0.75 | 7.5 |
| Sodium Metabisulphite | 0.3 | 3.0 |
| Disodium Edetate, dihydrate | 0.1 | 1.0 |
| Methylparahydroxybenzoate | 0.2 | 2.0 |
| Propylparahydroxybenzoate | 0.04 | 0.4 |
| Disodium Hydrogen Orthophosphate, 12H$_2$O | 1.19 | 11.9 |
| Sodium Dihydrogen Orthophosphate, 2H$_2$O | 0.52 | 5.2 |
| Water | 63.9 | 639.0 |

EXAMPLE 4
25% 5-ASA FOAM CONCENTRATE
(without Addition of Propellant)

|  | % (w/w) | Weight (g) |
|---|---|---|
| 5-Aminosalicylic Acid | 25.0 | 42.5 |
| Propylene Glycol | 30.0 | 51.0 |
| Emulsifying Wax ('Polawax NF') | 2.0 | 3.4 |
| Sodium Metabisulphite | 0.3 | 0.51 |
| Disodium Edetate, dihydrate | 0.1 | 0.17 |
| Sodium Benzoate | 0.1 | 0.17 |

EXAMPLE 4
25% 5-ASA FOAM CONCENTRATE
(without Addition of Propellant)

|  | % (w/w) | Weight (g) |
|---|---|---|
| Disodium Hydrogen Orthophosphate, 12H2O | 1.0 | 1.7 |
| Sodium Dihydrogen Orthophosphate, 2H2O | 0.6 | 1.02 |
| Water | 35.95 | 61.115 |

EXAMPLE 5
25% 5-ASA FOAM

|  | % (w/w) | Weight (g) |
|---|---|---|
| 5-Aminosalicylic Acid | 25.0 | 250.0 |
| Polysorbate 80 | 0.25 | 2.50 |
| Emulsifying Wax ('Polawax NF') | 0.5 | 5.0 |
| Colloidal Silicon Dioxide ('Aerosil 200') | 0.5 | 5.0 |
| Sodium Metabisulphite | 0.3 | 3.0 |
| Disodium Edetate, dihydrate | 0.1 | 1.0 |
| Methylparahydroxybenzoate | 0.2 | 2.0 |
| Propylparahydroxybenzoate | 0.04 | 0.4 |
| Disodium Hydrogen Orthophosphate, 12H2O | 1.19 | 11.9 |
| Sodium Dihydrogen Orthophosphate, 2H2O | 0.52 | 5.2 |
| Glycerol | 15.0 | 150.0 |
| Macrogol 300 | 15.0 | 150.0 |
| Water, Deionised | 33.4 | 334.0 |
| Propellants 'Arcton 12/114' 40:60 | 8.0 | 80.0 |
|  | 100.0 | 100.0 |

EXAMPLE 6
22.5% 5-ASA FOAM

|  | % (w/w) | Weight (g) |
|---|---|---|
| 5-Aminosalicylic Acid | 22.50 | 2.475 |
| Polysorbate 20 (Tween 20) | 10.00 | 1.100 |
| Emulsifying Wax ('Polawax NF') | 0.40 | 0.044 |
| Colloidal Silicon Dioxide (Aerosil 200) | 0.40 | 0.044 |
| Sodium Metabisulphite | 0.30 | 0.033 |
| Disodium Edetate, dihydrate | 0.10 | 0.011 |
| Methylparahydroxybenzoate | 0.20 | 0.022 |
| Propylparahydroxybenzoate | 0.04 | 0.0044 |
| Disodium Hydrogen Orthophosphate, 12H2O | 1.19 | 0.131 |
| Sodium Dihydrogen Orthophosphate, 2H2O | 0.52 | 0.057 |
| Glycerol | 11.50 | 1.265 |
| Macrogol 300 | 11.50 | 1.265 |
| Water, Deionised | 31.35 | 3.44 |
| Propellants 'Arcton 12/114' 40:60 | 10.00 | 1.100 |
|  | 100.00 | 11.00 |

EXAMPLE 7
20% 5-ASA FOAM

|  | % (w/w) | Weight (g) |
|---|---|---|
| 5-Aminosalicylic Acid | 20.00 | 1.000 |
| Sorbitan Mono-oleate | 0.21 | 0.011 |
| Polysorbate 20 | 7.80 | 0.390 |
| Emulsifying Wax | 0.43 | 0.022 |
| Colloidal Silicon Dioxide | 0.43 | 0.022 |
| Sodium Metabisulphite | 0.26 | 0.013 |
| Disodium Edetate, dihydrate | 0.10 | 0.005 |
| Methylparahydroxybenzoate | 0.20 | 0.010 |
| Propylparahydroxybenzoate | 0.04 | 0.002 |
| Disodium Hydrogen Orthophosphate, 12H2O | 1.19 | 0.060 |
| Sodium Dihydrogen Orthophosphate, 2H2O | 0.52 | 0.026 |
| Glycerol | 12.75 | 0.638 |
| Macrogol 300 | 12.75 | 0.638 |
| Water, Deionised | 33.32 | 1.666 |
| Propellants 'Arcton 12/114' 40:60 | 10.00 | 0.500 |
|  | 100.00 | 5.000 |

What is claimed is:

1. A pharmaceutical composition suitable for intrarectal administration in the form of a foam, which comprises a therapeutically effective amount of 5-aminosalicylic acid, a pharmaceutically acceptable aqueous carrier therefore which carrier contains water in an amount from about 20% (w/w) to about 100% (w/w) and a water-soluble organic polyalcohol selected from propylene glycol, glycerol and a polyethylene glycol and mixtures thereof, in an amount from 0% (w/w) to 80% (w/w) of the carrier, an emulsifying wax in an amount up to 2% (w/w) of the composition, and a liquid or liquified gas propellant, wherein the 5-aminosalicylic acid is present in an amount corresponding to at least 15% (w/w) of the composition.

2. A composition according to claim 1 wherein the 5-aminosalicyclic acid is present in an amount, between 18% and 30% (w/w) of the composition.

3. A composition according to claim 1 wherein the particle size of the 5-aminosalicylic acid is such that at least 95% of the particles have an equivalent sphere diameter of less than 60μ.

4. A composition according to claim 1 wherein the carrier is a mixture of water and a water-soluble polyalcohol such as propylene glycol, glycerol, or a polyethyleneglycol.

5. A composition according to claim 1 which contains a non-ionic emulsifying wax in an amount corresponding to up to 2% (w/w) of the composition.

6. A composition according to claim 1 which contains colloidal silica in an amount corresponding to up to 1% (w/w) of the composition.

7. An aerosol container used with a suitable metering valve for dispensing a foam intrarectally, containing a composition as defined in claim 1.

* * * * *